United States Patent
Song et al.

(10) Patent No.: US 8,306,296 B2
(45) Date of Patent: Nov. 6, 2012

(54) CLUTTER SIGNAL FILTERING USING EIGENVECTORS IN AN ULTRASOUND SYSTEM

(75) Inventors: Seong Ho Song, Suwon-si (KR); Tae Yun Kim, Seoul (KR)

(73) Assignee: Medison Co., Ltd., Kangwon-do (KR)

( * ) Notice: Subject to any disclaimer, the term of this patent is extended or adjusted under 35 U.S.C. 154(b) by 371 days.

(21) Appl. No.: 12/769,411

(22) Filed: Apr. 28, 2010

(65) Prior Publication Data
US 2010/0280384 A1  Nov. 4, 2010

(30) Foreign Application Priority Data

Apr. 30, 2009 (KR) .................. 10-2009-0038079
Dec. 22, 2009 (KR) .................. 10-2009-0128886

(51) Int. Cl.
*G06K 9/00* (2006.01)
*A61B 8/00* (2006.01)
(52) U.S. Cl. ............... 382/128; 600/437; 128/200.16
(58) Field of Classification Search .............. None
See application file for complete search history.

(56) References Cited

U.S. PATENT DOCUMENTS

| | | | | |
|---|---|---|---|---|
| 4,137,532 A | * | 1/1979 | Taylor et al. | 342/93 |
| 5,086,775 A | * | 2/1992 | Parker et al. | 600/453 |
| 5,379,770 A | * | 1/1995 | Van Veen | 600/455 |
| 5,490,516 A | * | 2/1996 | Hutson | 600/508 |
| 5,601,084 A | * | 2/1997 | Sheehan et al. | 600/450 |
| 5,823,964 A | * | 10/1998 | Liu et al. | 600/454 |
| 5,910,118 A | | 6/1999 | Kanda et al. | |
| 5,978,646 A | * | 11/1999 | Weinberg | 434/6 |
| 6,690,816 B2 | * | 2/2004 | Aylward et al. | 382/128 |
| 6,705,993 B2 | * | 3/2004 | Ebbini et al. | 600/443 |
| 6,733,454 B1 | * | 5/2004 | Bakircioglu et al. | 600/453 |
| 7,450,746 B2 | * | 11/2008 | Yang et al. | 382/131 |
| 8,202,221 B2 | * | 6/2012 | Osumi et al. | 600/443 |
| 2002/0102023 A1 | * | 8/2002 | Yamauchi | 382/199 |
| 2003/0069504 A1 | | 4/2003 | Wilkening et al. | |
| 2005/0276506 A1 | | 12/2005 | Kwon et al. | |
| 2006/0184021 A1 | | 8/2006 | Kim et al. | |
| 2007/0116373 A1 | * | 5/2007 | Hwang et al. | 382/261 |

(Continued)

FOREIGN PATENT DOCUMENTS

JP       10-099333       4/1998

(Continued)

OTHER PUBLICATIONS

Extended European Search Report for EP 10161384.2-2319, 9 pages, mailed Aug. 5, 2010.

(Continued)

*Primary Examiner* — Manav Seth
(74) *Attorney, Agent, or Firm* — McDermott Will & Emery LLP (57) ABSTRACT

Embodiments for setting eigenvectors for clutter signal filtering from Doppler signals in an ultrasound system are disclosed. In one embodiment, the ultrasound system includes: a Doppler signal acquisition unit configured to transmit and receive ultrasound signals to and from a target object to acquire first Doppler signals; and a processing unit configured to compute a plurality of eigenvectors by using the first Doppler signals and form second Doppler signals corresponding to directions of the computed eigenvectors, the processing unit being further configured to compute component values of the second Doppler signals and set eigenvectors for clutter signal filtering among the plurality of eigenvectors by using the computed component values.

19 Claims, 6 Drawing Sheets

U.S. PATENT DOCUMENTS

| | | | |
|---|---|---|---|
| 2008/0181479 A1* | 7/2008 | Yang et al. | 382/131 |
| 2010/0228129 A1* | 9/2010 | Osumi | 600/443 |
| 2011/0026796 A1* | 2/2011 | Hyun et al. | 382/131 |

FOREIGN PATENT DOCUMENTS

| | | |
|---|---|---|
| JP | 2006-149596 | 6/2006 |
| JP | 2006-204912 | 8/2006 |
| KR | 10-2005-0117011 A | 12/2005 |
| KR | 10-2007-0056137 A | 5/2007 |
| KR | 10-2009-0041475 A | 4/2009 |
| WO | WO 2007/001352 | 1/2007 |

OTHER PUBLICATIONS

Elnokrashy et al., "Nonparametric Clutter Rejection in Doppler Ultrasound Using Principal Component Analysis," Medical Imaging 2003: Ultrasoic Imaging and Signal Processing, Proceedings of SPIE vol. 5035:258-264 (2003).

Bjaerum et al., "Clutter Filters Adapted to Tissue Motion in Ultrasound Color Flow Imaging," IEEE Transactions on Ultrasonics, Ferroelectrics, and Frequency Control, 49(6):693-704 (Jun. 2002).

Yu et al., "Eigen-Based Clutter Filters for Color Flow Imaging: Single-Ensemble vs. Multi Ensemble Approaches," 2007 IEEE Ultrasonics Symposium, pp. 1101-1104.

Yu, "Eigen-Based Signal Processing Methods for Ultrasound Color Flow Imaging," The Edward S. Rogers Sr. Department of Electrical and Computer Engineering, Collaborative Program with the Institute of Biomaterials & Biomedical Engineering, University of Toronto, 137 pages, Copyright by Alfred C.H. Yu 2007.

Korean Notice of Allowance, issued in Korean Patent Application No. 10-2009-0128886, dated Jan. 30, 2012.

* cited by examiner

CLUTTER SIGNAL FILTERING USING EIGENVECTORS IN AN ULTRASOUND SYSTEM

CROSS-REFERENCE TO RELATED APPLICATIONS

The present application claims priority from Korean Patent Application Nos. 10-2009-0038079 and 10-2009-0128886 filed on Apr. 30, 2009 and Dec. 22, 2009, respectively, the entire subject matters of which are incorporated herein by reference.

TECHNICAL FIELD

The present disclosure relates to ultrasound signal processing, and more particularly to clutter signal filtering upon Doppler signals using eigenvectors in an ultrasound system.

BACKGROUND

Recently, an ultrasound system has been extensively used in the medical field due to its non-invasive and non-destructive nature. Modern high-performance ultrasound imaging diagnostic systems and techniques are commonly used to produce two- or three-dimensional ultrasound images of internal features of patients. In order to provide the ultrasound images, the ultrasound system operates in various image modes such as a brightness mode, a Doppler mode and the like to acquire ultrasound images for diagnosis.

In the Doppler mode, the ultrasound system provides a color flow image visualizing velocities of moving objects such as blood flow, heart, etc. The color flow image may be formed based on Doppler signals obtained by alternately transmitting and receiving ultrasound signals to and from a target object at a pulse repetition frequency (PRF). The Doppler signals may include low frequency signals (the so-called clutter signals) due to the motion of a cardiac wall or valve of a heart. The clutter signals may have amplitudes, which are over 100 times than those of pure Doppler signals indicative of velocities of the blood flow. The clutter signals may be an obstacle to accurately detecting velocities of the blood flow. Thus, it is required to remove the clutter signals from the Doppler signals for accurate velocity detection of the blood flow. Since the eigenvector-based clutter filtering is carried out by reflecting characteristics of the Doppler signals, the performance of the eigenvector-based clutter filtering may exceed that of the infinite impulse response filtering. Thus, it has been required to appropriately set eigenvectors for the improved eigenvector-based clutter filtering.

SUMMARY

Embodiments for setting eigenvectors for clutter signal filtering are disclosed herein. In one embodiment, by way of non-limiting example, an ultrasound system includes: a Doppler signal acquisition unit configured to transmit and receive ultrasound signals to and from a target object to acquire first Doppler signals; and a processing unit configured to compute a plurality of eigenvectors by using the first Doppler signals and form second Doppler signals corresponding to directions of the computed eigenvectors, the processing unit being further configured to compute component values of the second Doppler signals and set eigenvectors for clutter signal filtering among the plurality of eigenvectors by using the computed component values.

In another embodiment, a method of setting eigenvectors in an ultrasound system providing a color flow image, comprises: a) transmitting and receiving ultrasound signals to and from a target object to acquire first Doppler signals; b) computing a plurality of eigenvectors by using the first Doppler signals; c) forming second Doppler signals corresponding to directions of the computed eigenvectors and computing component values of the second Doppler signals; and d) setting eigenvectors for clutter signal filtering among the plurality of eigenvectors by using the computed component values.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
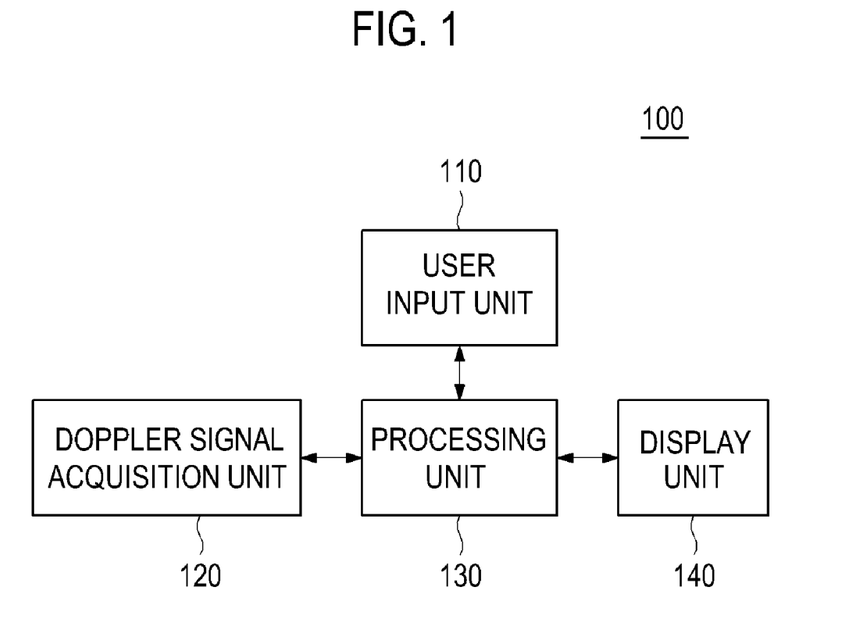
FIG. 1 is a block diagram showing an illustrative embodiment of an ultrasound system

Referring to FIG. 1, an illustrative embodiment of an ultrasound system 100 is shown. As depicted therein, the ultrasound system 100 may include a user input unit 110. The user input unit 110 may allow a user to input a user instruction. The user instruction may include information on the position and size of a region of interest (ROI) (e.g., a color box), which the user wants to set on a brightness mode (B-mode) image. The user input unit 110 may include at least one of a control panel, a mouse, a keyboard, a touch screen, etc.

The ultrasound system 100 may further include a Doppler signal acquisition unit 120. The Doppler signal acquisition unit 120 may be operable to alternately transmit and receive ultrasound signals to and from a target object (e.g., heart, blood flow, etc) in synchronization with a pulse repetition frequency (PRF). The Doppler signal acquisition unit 120 may acquire Doppler signals corresponding to the ROI based on the received ultrasound signals. The acquisition of the Doppler signals will be described in detail by referring to FIG. 2.

Figure 2:
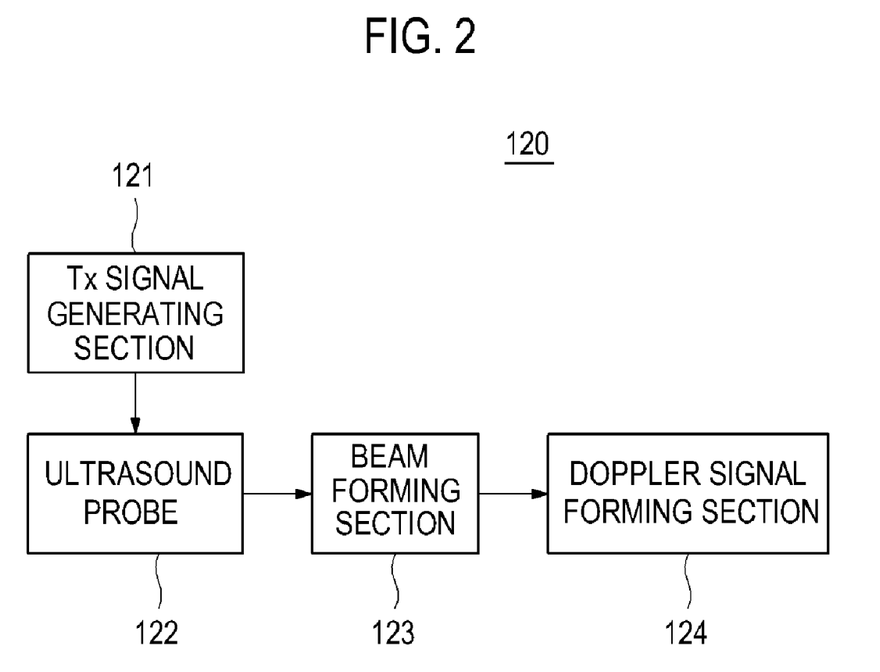
FIG. 2 is a block diagram showing an illustrative embodiment of a Doppler signal acquisition unit shown in FIG. 1.

FIG. 2 is a block diagram showing an illustrative embodiment of the Doppler signal acquisition unit 120. Referring to FIG. 2, the Doppler signal acquisition unit 120 may include a transmit (Tx) signal generating section 121. The Tx signal generating section 121 may be operable to generate a plurality of Tx signals. The generation of the Tx signals may be controlled by whether the current image mode is a B-mode, a C-mode, a D-mode, etc. In one embodiment, the Tx signal generating section 121 may generate Tx signals for forming a color flow image within the ROI consisting of a plurality of scan lines in the C-mode. The Tx signal generating section 121 may repeatedly generate the Tx signals based on a predetermined ensemble number.

The Doppler signal acquisition unit 120 may further include an ultrasound probe 122 containing a plurality of elements for reciprocally converting ultrasound signals and electrical signals. The ultrasound probe 122 may be operable to transmit ultrasound signals into a target object in response to the Tx signals. The ultrasound probe 122 may be further operable to receive echo signals reflected from the target object to thereby output electrical receive signals, which are analog signals. The transmission and reception of the ultrasound signals are alternately carried out to output a plurality of electrical receive signals.

The Doppler signal acquisition unit 120 may further include a beam forming section 123. The beam forming section 123 may be operable to convert the electrical receive signals into digital signals. The beam forming section 123 may be further operable to apply delays to the digital signals in consideration of distances between the elements and focal points, thereby outputting digital receive-focused signals.

The Doppler signal acquisition unit 120 may further include a Doppler signal forming section 124 that may be operable to form Doppler signals based on the digital receive-focused signals. In one embodiment, the Doppler signals may include in-phase Doppler signals and quadrature phase signals. The Doppler signals may also include clutter signals. Hereinafter, these Doppler signals may be referred to as "first Doppler signals." The Doppler signal acquisition unit 120 may form the first Doppler signals up to the predetermined ensemble number for each of the scan lines within the ROI.

The ultrasound system 100 may further include a processing unit 130 coupled to the Doppler signal acquisition unit 120. The processing unit 130 may be operable to set at least one eigenvector based on the first Doppler signals. The processing unit 130 may be further operable to perform clutter signal filtering upon the first Doppler signals by using eigenvectors thereof to remove the clutter signals. The processing unit 130 may be operable to form a color flow image by using the Doppler signals from which the clutter signals are filtered out. The operation of the processing unit 130 will be described in detail by referring to FIG. 3.

Figure 3:
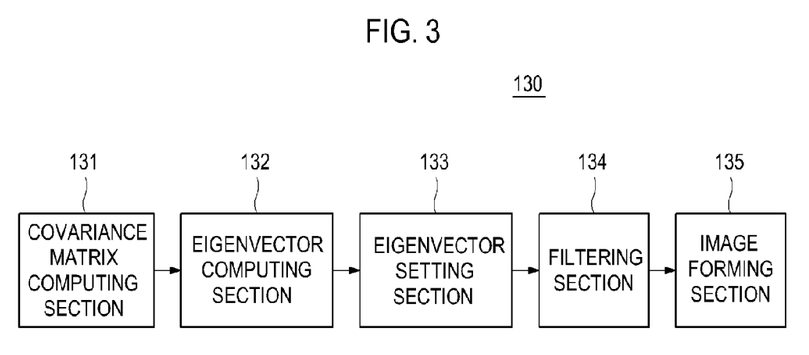
FIG. 3 is a block diagram showing an illustrative embodiment of a processing unit shown in FIG. 1.

FIG. 3 is a block diagram showing an illustrative embodiment of the processing unit 130. Referring to FIG. 3, the processing unit 130 may include a covariance matrix computing section 131. The covariance matrix computing section 131 may be operable to compute a covariance matrix by using the plurality of first Doppler signals provided from the Doppler signal acquisition unit 120. In one embodiment, the covariance matrix computing section 131 may be operable to select one of the scan lines, which are included in the ROI, and compute the covariance matrix by using the first Doppler signals corresponding to all of the pixels on the selected scan line. In another embodiment, the covariance matrix computing section 131 may be operable to select one of the scan lines, and compute the covariance matrix by using the first Doppler signals corresponding to a predetermined number of pixels on the selected scan line. In yet another embodiment, the covariance matrix computing section 131 may be operable to compute the covariance matrix by using the first Doppler signals corresponding to the entire pixels of the scan lines on the ROI. The covariance matrix may be computed by using various well-known methods. Thus, the detailed descriptions thereof will be omitted herein.

For the sake of convenience, a method of computing the covariance matrix by using the first Doppler signals corresponding to the entire pixels on the selected one scan line will be described. The processing unit 130 may further include an eigenvector computing section 132. The eigenvector computing section 132 may be operable to compute a plurality of eigenvalues by using the computed covariance matrix and eigenvectors corresponding to the respective eigenvalues. The eigenvalues and eigenvectors may be computed by using various well-known methods. As such, the detailed explanations thereof will be omitted herein.

The processing unit 130 may further include an eigenvector setting section 133. The eigenvector setting section 133 may be operable to set at least one eigenvector for performing clutter signal filtering upon the first Doppler signals by using the plurality of eigenvectors (or both eigenvalues and eigenvectors). In one embodiment, the eigenvector setting section 133 may project the first Doppler signals corresponding to the respective pixels on the selected scan line along the respective eigenvectors. Hereinafter, the projected first Doppler signals will be referred to as "second Doppler signals." The second Doppler signals may be obtained as many as the number of the eigenvectors. The eigenvector setting section 133 may be operable to compute component values from the second Doppler signals for the respective pixels. In one embodiment, the component values may be projected values of the second Doppler signals along the respective eigenvectors. The component values ($C_{ij}$) may be computed by using the following equation.

$$C_{ij}=S_i{}^{*}e_j \qquad (1)$$

wherein $S_i$ represents a first Doppler signal corresponding to an $i^{th}$ pixel and $e_j$ represents a $j^{th}$ eigenvector.

For example, the eigenvector setting section 133 may be operable to compute an inner product through the equation (1) for the first Doppler signals corresponding to the respective pixels on the selected scan line and eigenvectors $e_1$-$e_{10}$ computed in the eigenvector computing section 132, thereby computing the component values of the second Doppler signals for the respective pixels. The eigenvector setting section 133 may be further operable to compute correlation values between the component values of the first Doppler signals and the component values of the second Doppler signals (i.e., amplitudes of the first and second Doppler signals). The eigenvector setting section 133 may compare the computed correlation values with a predetermined threshold to detect the component values of the second Doppler signals greater than the predetermined threshold. The eigenvector setting section 133 may be operable to set the eigenvectors corresponding to the detected component values as eigenvectors for clutter signal filtering.

Figure 4:
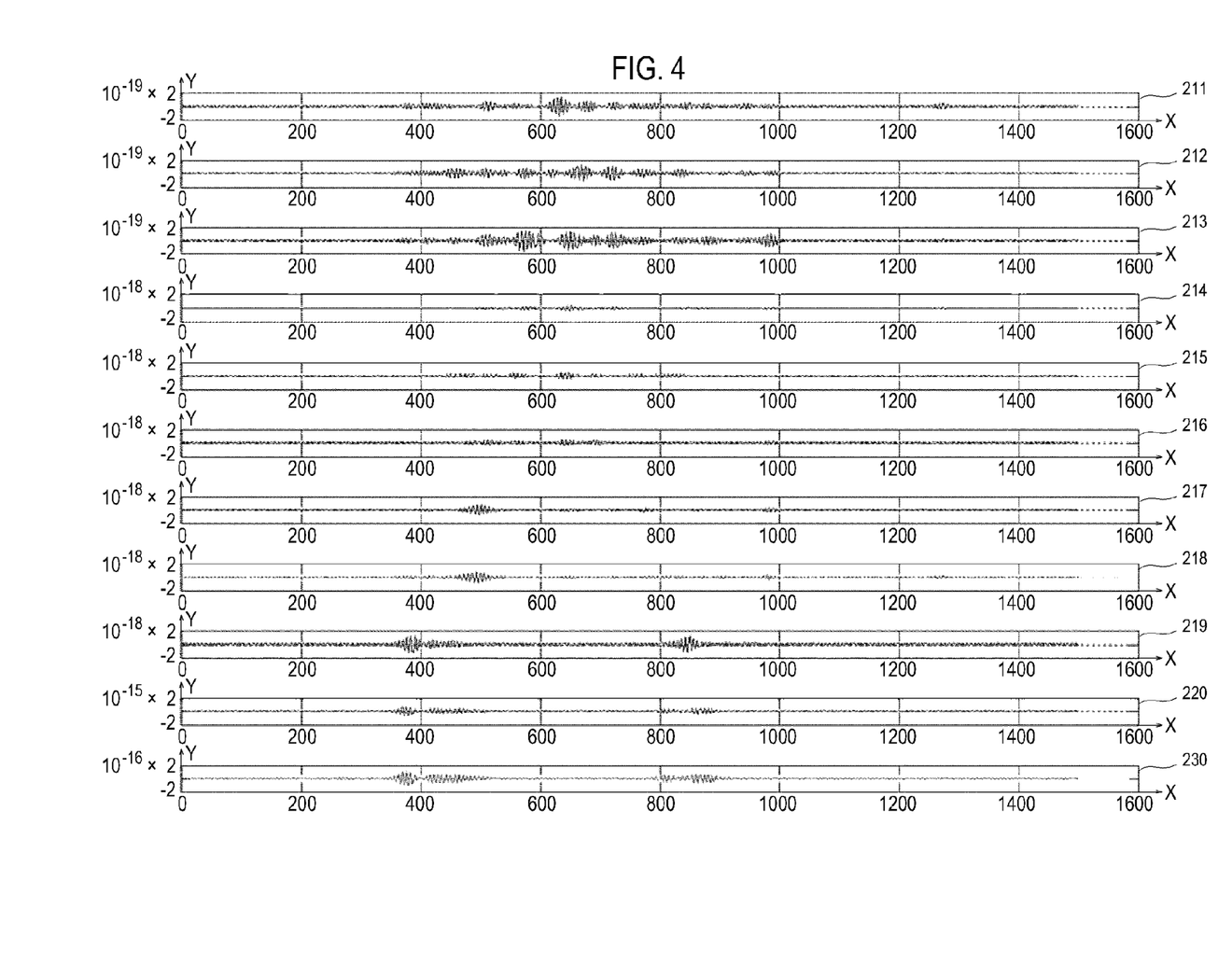
FIG. 4 shows graphs indicative of component values of the Doppler signals.

FIG. 4 shows graphs indicative of component values of the Doppler signals. In FIG. 4, reference numerals "211-220" show graphs indicative of component values of the second Doppler signals (hereinafter, referred to as "first component graphs"). Further, reference numeral "230" shows a graph indicative of component values of the first Doppler signals (hereinafter, referred to as "second component graph"). In FIG. 4, a horizontal direction (X-axis) represents positions of the pixels (i.e., depths) and a vertical direction (Y-axis) represents the component values (i.e., amplitudes) of the Doppler signals. The portions of relatively large component values may correspond to blood vessels, which may be a possible source of the clutter signals.

As such, in one embodiment, the eigenvector setting section 133 may be operable to detect the component values of the second Doppler signals whose correlation values are greater than the predetermined threshold (e.g., the component values corresponding to first graphs 219 and 220 in FIG. 4). The eigenvector setting section 133 may be further operable to set eigenvectors corresponding to the component values $e_9$-$e_{10}$ of the detected second Doppler signals as the eigenvectors for the clutter signal filtering.

Figure 5:
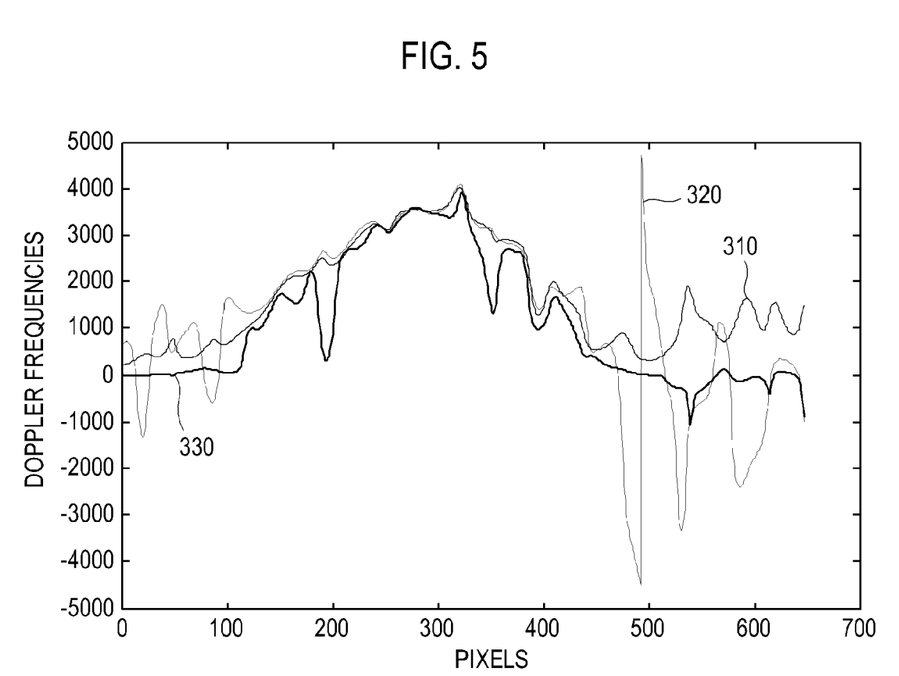
FIG. 5 is a graph showing Doppler frequency estimates of the Doppler signals.

FIG. 5 is a graph showing Doppler frequency estimates of the Doppler signals. In FIG. 5, reference numeral "310" represents Doppler frequencies of original Doppler signals obtained at a vessel portion (i.e., first Doppler signals). Further, reference numeral "320" represents Doppler frequencies of the Doppler signals resulting from the clutter signal filtering upon the first Doppler signals using the eigenvectors $e_9$ and $e_{10}$, which are set in the eigenvector setting section 133. Reference numeral "330" represents Doppler frequencies of the Doppler signals resulting from the clutter signal filtering upon the first Doppler signals using the eigenvector $e_{10}$, which has been set in the eigenvector setting section 133. As shown in FIG. 5, the clutter signal filtering using the eigenvectors $e_9$ and $e_{10}$ has a better performance than the clutter signal filtering using the eigenvector $e_{10}$.

In another embodiment, the eigenvector setting section 133 may be operable to perform the clutter signal filtering upon the first Doppler signals by sequentially using the eigenvectors computed in the eigenvector computing section 132 to thereby form clutter signal filtered Doppler signals (hereinafter, referred to as "third Doppler signals"). In this case, the first Doppler signals may be filtered in an order determined by the magnitudes of the eigenvalues of the respective eigenvectors. The eigenvector setting section 133 may be further operable to compute component values of the third Doppler signals for each of the pixels. In one embodiment, by way of non-limiting example, the component values may be a phase difference between third Doppler signals corresponding to an $n^{th}$ sample (or ensemble) and a $(n+1)^{th}$ sample (or ensemble) at each of the pixels, wherein n is a positive integer equal to or greater than 1. The eigenvector setting section 133 may be further operable to set eigenvectors for clutter signal filtering by using the computed component values. The eigenvector setting section 133 may be operable to set an eigenvector, which makes the phase difference kept to have the same sign, as the eigenvector for the clutter signal filtering.

For example, assuming that blood flows at a constant velocity during a scanning time, the phase differences of the Doppler signals may not be changed. That is, the phase differences may be maintained to have the same sign. The eigenvector setting section 133 may be operable to perform the clutter signal filtering upon the first Doppler signals by using the eigenvector having the largest eigenvalue (e.g., eigenvector $e_{10}$) among the plurality of eigenvectors $e_1$ to $e_{10}$ to form the third Doppler signals. The eigenvector setting section 133 may be further operable to compute phase differences between the third Doppler signals corresponding to an $n^{th}$ sample (or ensemble) and a $(n+1)^{th}$ sample (or ensemble) for each of the pixels. The eigenvector setting section 133 may be operable to detect a sign change of the detected phase differences. If the detected sign change is not maintained in the same sign, i.e., the sign is changed from plus (+) to minus (−) or vice versa, then the clutter signal filtering may be performed upon the first Doppler signals by using the eigenvectors having the first and second largest eigenvalues, e.g., eigenvectors $e_{10}$ and $e_9$ to form the third Doppler signals. Thereafter, the eigenvector setting section 133 may be operable to detect a sign change of the phase differences for the third Doppler signals in the same manner described above.

Figure 6:
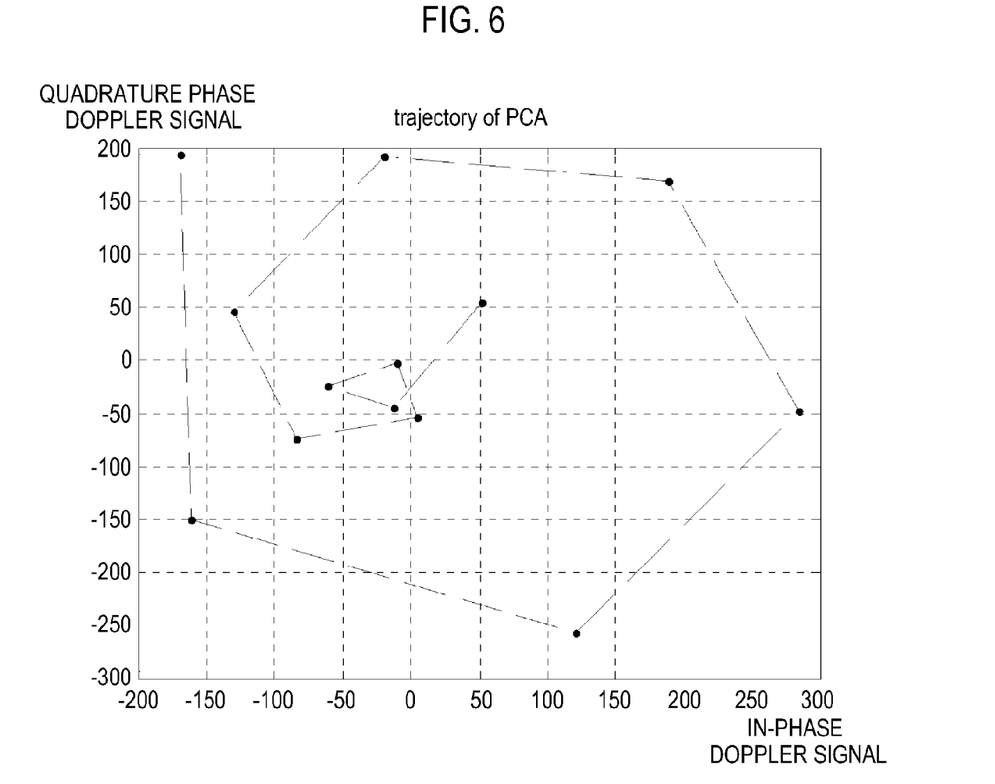
FIG. 6 is a graph showing a trajectory of the phase differences computed from the third Doppler signals, which are clutter signals filtered by using two eigenvectors.

FIG. 6 is a graph showing a trajectory of the phase differences of the third Doppler signals, in which the clutter signals are filtered by using two eigenvectors $e_9$ and $e_{10}$. If the sign change of the detected phase differences is not maintained in the same sign, as shown in TABLE 1, then the eigenvector setting section 133 may be operable to perform the clutter signal filtering upon the first Doppler signals by using the eigenvectors having the first to third largest eigenvalues, e.g., eigenvectors $e_8$-$e_{10}$, to form the third Doppler signals. Thereafter, the eigenvector setting section 133 may detect a sign change of the phase differences for the third Doppler signals.

TABLE 1

| Sign change of phase differences | |
|---|---|
| Filtering with eigenvectors $e_9$ and $e_{10}$ | Filtering with eigenvectors $e_8$ to $e_{10}$ |
| − − + − − ... − − | − − − − − − − − ... − − − |

Figure 7:
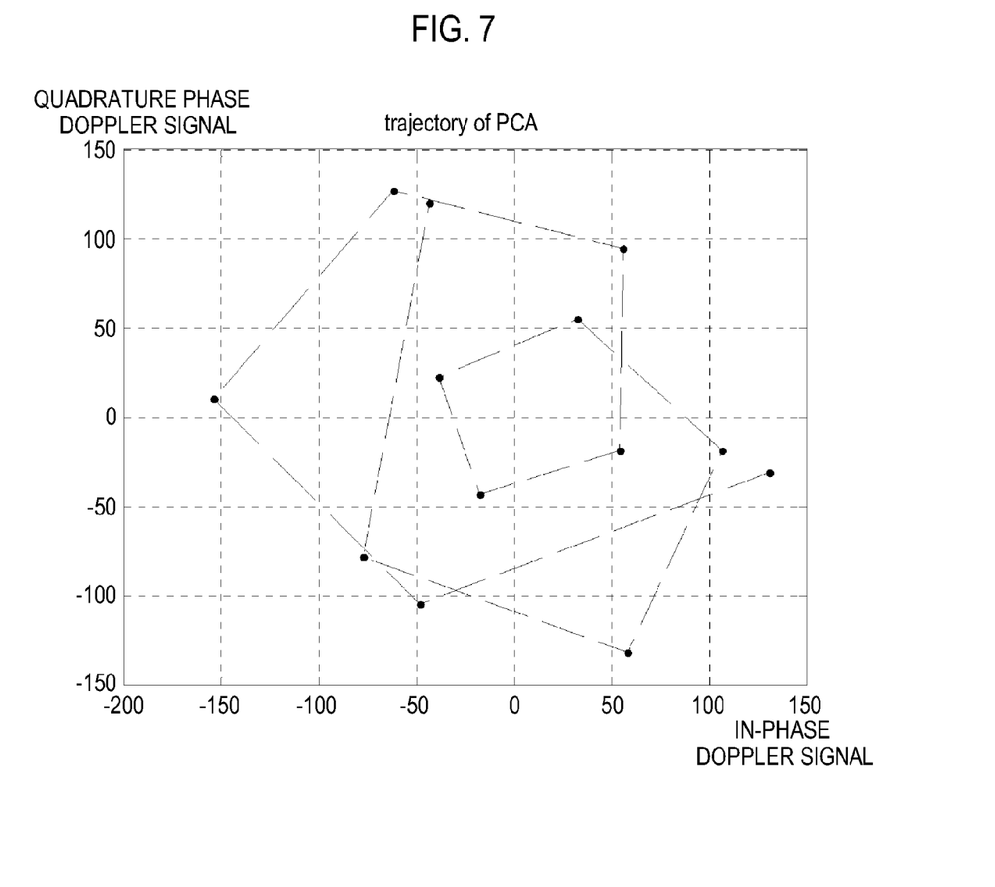
FIG. 7 is a graph showing a trajectory of the phase differences computed from the third Doppler signals, which are clutter signals filtered by using three eigenvectors.

FIG. 7 is a graph showing a trajectory of phase differences of the third Doppler signals, in which the clutter signals are filtered by using the three eigenvectors $e_8$ to $e_{10}$. If it is determined that the sign change of the detected phase differences is maintained in the same sign, i.e., the sign of the phase differences is not changed, then the eigenvector setting section 133 may set the eigenvectors of the eigenvectors $e_8$ to $e_{10}$ as the eigenvectors for the clutter signal filtering. In FIGS. 6 and 7, PCA represents an abbreviation of Principal Component Analysis.

In one embodiment, although it is described above that the eigenvectors for the clutter signal filtering are set by using the eigenvectors in a magnitude order of the eigenvalues of the entire eigenvectors in order to detect the sign change of the phase differences, the setting of the eigenvectors for the clutter signal filtering may not be limited thereto. In another embodiment, the eigenvectors for the clutter signal filtering may be set by using the eigenvectors in a magnitude order of the eigenvalues of the eigenvectors corresponding to the component values $e_9$-$e_{10}$ of the detected second Doppler signals in FIG. 4.

The processing unit 130 may further include a filtering section 134. The filtering section may be operable to perform the clutter signal filtering upon the first Doppler signals by using the eigenvectors set in the eigenvector setting section 133. The processing unit 130 may further include an image forming section 135. The image forming section 135 may be operable to form a color flow image by using the Doppler signals with the clutter signals filtered.

The ultrasound system 100 may further include a display unit 140. The display unit 140 may be embodied with any display capable of displaying the ultrasound images such as a B-mode image, a color flow image and the like. In one embodiment, the display unit 140 may include at least one of a CRT monitor, a LCD monitor and the like.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   a Doppler signal acquisition unit configured to transmit and receive ultrasound signals to and from a target object to acquire first Doppler signals; and
   a processing unit configured to compute a plurality of eigenvectors by using the first Doppler signals and form second Doppler signals corresponding to directions of the computed eigenvectors, the processing unit being further configured to compute component values of the second Doppler signals and set eigenvectors for clutter signal filtering among the plurality of eigenvectors by using the computed component values.

2. The ultrasound system of claim 1, wherein the component values include amplitudes of the second Doppler signals.

3. The ultrasound system of claim 1, wherein the processing unit includes:
   a covariance matrix computing section configured to compute a covariance matrix by using the first Doppler signals;
   an eigenvector computing section configured to compute the plurality of eigenvectors based on the computed covariance matrix; and
   an eigenvector setting section configured to compute inner product for the first Doppler signals and the plurality of eigenvectors to compute the component values of the second Doppler signals for respective eigenvector directions and set the eigenvectors for the clutter signal filtering among the plurality of eigenvectors based on component values of the first Doppler signals and the component values of the second Doppler signals.

4. The ultrasound system of claim 3, wherein the eigenvector setting section is configured to:
   compute correlation between the component values of the first Doppler signals and the component values of the second Doppler signals,
   detect the component values of the second Doppler signals whose correlation is greater than a predetermined threshold, and
   set the eigenvectors corresponding to the detected component values of the second Doppler signals as the eigenvectors for the clutter signal filtering.

5. The ultrasound system of claim 4, wherein the processing unit further includes:
   a filtering section configured to perform the clutter signal filtering upon the plurality of first Doppler signals by using the eigenvectors for the clutter signal filtering; and
   an image forming section configured to form a color flow image based on the clutter signal filtered Doppler signals.

6. The ultrasound system of claim 1, wherein the component values include phase differences.

7. The ultrasound system of claim 6, wherein the processing unit includes:

a covariance matrix computing section configured to compute a covariance matrix by using the first Doppler signals;
an eigenvector computing section configured to compute the plurality of eigenvectors based on the computed covariance matrix; and
an eigenvector setting section configured to compute inner product for the first Doppler signals and the plurality of eigenvectors to compute the component values of the second Doppler signals for respective eigenvector directions and set the eigenvectors for the clutter signal filtering among the plurality of eigenvectors based on component values of the first Doppler signals and the component values of the second Doppler signals.

8. The ultrasound system of claim 7, wherein the eigenvector setting section is configured to:
   compute phase differences between $n^{th}$ samples and $(n+1)^{th}$ samples of the second Doppler signals, wherein n is a positive integer greater than 1, and
   detect a sign change of the computed phase differences to set the eigenvectors of which the sign change of the phase differences uniformly maintains as the eigenvectors for the clutter signal filtering.

9. The ultrasound system of claim 8, wherein the processing unit further includes:
   a filtering section configured to perform the clutter signal filtering upon the plurality of first Doppler signals by using the eigenvectors for the clutter signal filtering; and
   an image forming section configured to form a color flow image based on the clutter signal filtered Doppler signals.

10. A method of setting eigenvectors in an ultrasound system providing a color flow image, comprising:
    a) transmitting and receiving ultrasound signals to and from a target object to acquire first Doppler signals;
    b) computing a plurality of eigenvectors by using the first Doppler signals;
    c) forming second Doppler signals corresponding to directions of the computed eigenvectors and computing component values of the second Doppler signals; and
    d) setting eigenvectors for clutter signal filtering among the plurality of eigenvectors by using the computed component values.

11. The method of claim 10, wherein the step b) includes:
    computing covariance matrixes by using the first Doppler signals: and
    computing the plurality of eigenvectors by using the covariance matrixes.

12. The method of claim 10, wherein the component values include amplitudes of the second Doppler signals.

13. The method of claim 12, wherein the step c) includes computing an inner product between the first Doppler signals and the plurality of eigenvectors to compute the component values of the second Doppler signals in respective directions of the eigenvectors.

14. The method of claim 13, wherein the step d) includes:
    computing correlation between the component values of the first Doppler signals and the component values of the second Doppler signals;
    detecting the component values of the second Doppler signals whose correlation is greater than a predetermined threshold; and
    setting the eigenvectors corresponding to the detected component values of the second Doppler signals as the eigenvectors for the clutter signal filtering.

15. The method of claim 14, further comprising:
e) performing the clutter signal filtering upon the plurality of first Doppler signals by using the eigenvectors for the clutter signal filtering;
f) forming a color flow image based on the clutter signal filtered Doppler signals; and
g) displaying the color flow image.

16. The method of claim 10, wherein the component values include phase differences.

17. The method of claim 16, wherein the step c) includes:
performing clutter signal filtering upon the first Doppler signals by using the plurality of eigenvectors according the magnitudes to form the second Doppler signals; and
computing phase differences between $n^{th}$ samples and $(n+1)^{th}$ samples of the second Doppler signals, wherein n is a positive integer greater than 1.

18. The method of claim 17, wherein the step d) includes detecting a sign change of the computed phase differences to set the eigenvectors of which the sign change of the phase differences uniformly maintains as the eigenvectors for the clutter signal filtering.

19. The method of claim 18, further comprising:
e) performing the clutter signal filtering upon the plurality of first Doppler signals by using the eigenvectors for the clutter signal filtering;
f) forming a color flow image based on the clutter signal filtered Doppler signals; and
g) displaying the color flow image.

* * * * *